United States Patent [19]

Tang

[11] Patent Number: 4,515,929

[45] Date of Patent: May 7, 1985

[54] PEROXIDE COMPOSITION

[75] Inventor: Robert H. Tang, Norton, Ohio

[73] Assignee: PPG Industries, Inc., Pittsburgh, Pa.

[21] Appl. No.: 518,162

[22] Filed: Jul. 28, 1983

[51] Int. Cl.$^3$ .................. C01B 13/00; C01B 15/00; C09K 3/00; C08F 4/38
[52] U.S. Cl. .................. 526/228; 252/186.26
[58] Field of Search .................. 526/228, 230.5; 252/186.26

[56] References Cited

U.S. PATENT DOCUMENTS

| | | | |
|---|---|---|---|
| 3,022,282 | 2/1962 | Marous et al. | 526/230.5 |
| 3,637,633 | 1/1972 | Dixon et al. | 526/228 |
| 3,825,509 | 7/1974 | Miller | 260/86.3 |
| 3,988,261 | 10/1976 | Barter et al. | 252/431 |
| 4,039,475 | 8/1977 | Oosterwijk et al. | 252/431 R |
| 4,092,470 | 5/1978 | Oosterwijk et al. | 526/227 |
| 4,335,230 | 6/1982 | Kolczynski et al. | 526/228 |
| 4,361,688 | 11/1982 | Halle et al. | 526/230.5 |

FOREIGN PATENT DOCUMENTS 32757  7/1981  European Pat. Off. .

Primary Examiner—Joseph L. Schofer
Assistant Examiner—Peter F. Kulkosky
Attorney, Agent, or Firm—Irwin M. Stein

[57] ABSTRACT

Dispersions of organic peroxide, e.g., organic peroxydicarbonates, in an aqueous medium are stabilized against homolytic peroxide decomposition at temperatures of from about $-5°$ C. to $20°$ C. by incorporating into the dispersion, e.g., into the organic peroxide phase, from about 0.05 to about 1 mole percent, basis the organic peroxide, of diphenyl peroxydicarbonate or di(alkyl substituted) phenyl peroxydicarbonate.

22 Claims, No Drawings

PEROXIDE COMPOSITION

DESCRIPTION OF THE INVENTION

The present invention relates to organic peroxide dispersions in an aqueous medium which are stabilized against peroxide decomposition at storage temperatures of from about −5° C. to about 20° C. and the use of such liquid organic peroxide compositions for the polymerization of ethylenically unsaturated monomers.

The polymerization of ethylenically unsaturated materials susceptible to free-radical polymerization, e.g., unsaturated vinyl-type monomers, such as vinyl chloride, with organic peroxides is well-documented in the literature. The polymeric products produced from such polymerizations have found extensive commercial applications. Much of the polymerization of vinyl halides, such as vinyl chloride, vinyl bromide or vinyl fluoride (or the copolymerization of such vinyl halides with vinylidene halides such as vinylidene chloride, vinylidene fluoride or other terminal vinyl-unsaturated containing compounds) is conducted in an aqueous medium, i.e., as an emulsion or suspension polymerization. In such polymerizations, the monomer or mixture of monomers to be polymerized is dispersed in water in the presence of a surfactant and thereafter the polymerization initiated with an organic peroxide.

Addition of the organic peroxide to the aqueous polymerization medium has been accomplished by various techniques. For example, a predetermined amount of peroxide, either as neat (undiluted) peroxide or diluted with a solvent, such as mineral spirits, is charged to the polymerization vessel together with the polymerizable monomer. The peroxide can be charged simultaneously with, prior to or subsequent to the addition of the monomer. Recently, it has been proposed to charge the organic peroxide to the polymerization reactor as an aqueous emulsion or suspension.

U.S. Pat. No. 3,825,509 describes a process for the suspension polymerization of vinyl chloride wherein the organic peroxide initiator is charged to the polymerization vessel as an aqueous emulsion in which the peroxide is present in the emulsion in an amount up to 19 weight percent. The surfactant used to prepare such aqueous peroxide emulsion is a combination of polyvinyl alcohol and polyoxyethylene sorbitan monolaurate. Emulsions containing greater than about 19 percent by weight of organic peroxide are described as being too viscous and, therefore, difficult to handle.

U.S. Pat. No. 3,988,261 describes the preparation of frozen aqueous organic peroxide emulsions which exhibit stability to freeze-thaw cycling. The emulsion can comprise from about 30–75 weight percent of the organic peroxide and, when frozen, provides a safe, physical form for storing, handling and shipping the organic peroxide.

U.S. Pat. No. 4,039,475 describes aqueous suspensions of organic peroxides, which peroxides are solid at about 20° C. The aqueous suspension contains a combination of nonionic emulsifiers, or nonionic and anionic emulsifiers, which permits the preparation of an aqueous suspension of solid organic peroxides in which the peroxide is present in amounts of from about 20 to about 50 weight percent. In order to prevent segregation of the solid peroxide from the suspending aqueous medium, thickeners are added to the suspension. Use of such aqueous suspensions for the aqueous suspension polymerization of a vinyl halide is described in U.S. Pat. No. 4,092,470.

European patent application No. 32,747 relates to aqueous emulsions of organic peroxides which are liquid at 5° C. More particularly, the aforesaid European patent application describes incorporating between 2 and 20 weight percent of an alkanol having from 1 to 4 carbon atoms and/or an alkanediol having from 2 to 4 carbon atoms in said emulsion so as to maintain the peroxide emulsion in liquid form at temperatures of from 10° C. to 25° C.

A disadvantage of the use of aqueous peroxide emulsions, particularly peroxides which have a 10 hour half-life temperature (in benzene) of less than about 55° C., is their insufficient shelf life when maintained at temperatures significantly above −5° C., e.g., above 0° C. When the aqueous matrix is frozen, the shelf life of liquid peroxydicarbonates is relatively good, but active oxygen is still lost slowly, e.g., a forty weight percent emulsion of di-secondarybutyl peroxydicarbonate (SBP) stored at −4° C. loses only about 4.25% of its original active oxygen after ten weeks storage. At 0° C., a forty weight percent SBP aqueous emulsion loses about 20 percent of its original active oxygen after ten weeks storage; whereas a forty weight percent SBP solution in mineral spirits loses about 4 percent of its original active oxygen after ten weeks storage at 0° C. Table I of U.S. Pat. No. 3,988,261 reports that a forty weight percent emulsion of SBP loses about 50 percent of its active oxygen after about 15 days when stored at 10° C. In contrast, a 40 weight percent solution in mineral spirits of SBP loses less than seven percent of its active oxygen after 14 days storage at that temperature.

It has now been discovered that the shelf life of liquid dispersions of aqueous peroxides when stored at −5° C. to +20° C. can be improved by incorporating within the emulsion a stabilizing amount of a diphenyl peroxydicarbonate. In particular, between about 0.1 and about 1 mole percent of the diphenyl peroxydicarbonate, based on the organic peroxide, is incorporated into the aqueous dispersion. Stabilizing amounts of this peroxydicarbonate reduce the rate of self induced homolytic decomposition of the peroxide. Diphenyl peroxydicarbonates contemplated for use as stabilizers or antioxidants in aqueous peroxide dispersions are diphenyl peroxydicarbonate and di(alkyl substituted) phenyl peroxydicarbonates.

DETAILED DESCRIPTION OF THE INVENTION

Diphenyl peroxydicarbonates contemplated herein as stabilizers or antioxidants to the aqueous organic peroxide dispersions described herein can be represented by the following graphic formula:

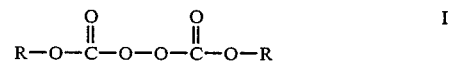

wherein R is phenyl or alkyl substituted phenyl. The alkyl group can contain from 1 to 4 carbon atoms, i.e., $C_1$–$C_4$ alkyl, and the phenyl radical can be substituted with from 1 to 3 of such alkyl groups.

The aforesaid diphenyl peroxydicarbonate stabilizers can be prepared by forming the chloroformate of phenol, or the corresponding alkyl substituted phenol, and reacting the chloroformate with aqueous sodium peroxide at low temperatures, e.g., 0° C.–10° C., as described in U.S. Pat. No. 2,370,588. Phenol and alkyl substituted phenols (hindered phenols) contemplated herein can be represented by the following graphic formula II and, more particularly, by the following graphic formula III:

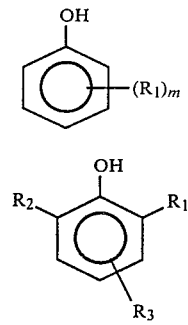

wherein $R_1$ is a $C_1$-$C_4$ alkyl group and m is zero (0) or the number 1, 2 or 3. When m is 1, the $C_1$-$C_4$ alkyl group bonded to the phenol nucleus can be in the ortho, meta or para position; but, is preferably in the ortho or para position. When m is 2, it is preferred that the alkyl substituents be at the two and six positions of the phenol nucleus; however, the alkyl groups can be substituted at the three and six, or the two and four positions. When m is 3, it is preferred that the alkyl groups are substituted at the two, four and six positions of the phenol nucleus; however, the alkyl groups can be substituted at the three, four and six positions. More particularly, when m is 3, the alkyl substituted phenols are represented by the graphic formula III wherein $R_1$, $R_2$ and $R_3$ are each $C_1$-$C_4$ alkyl groups. $R_3$ is preferably methyl and is preferably bonded to the phenol nucleus at the three or four positions, more preferably the four position. More preferably $R_1$ and $R_2$ are identical $C_1$-$C_3$ alkyl groups and $R_3$ is methyl.

Examples of alkyl substituted phenols include ortho-alkyl substituted phenol, meta-alkyl substituted phenol, para-alkyl substituted phenol, 2,6-dialkyl substituted phenol, 4-methyl-2-alkyl substituted phenol, and 4-methyl-2,6-dialkyl substituted phenol. As used herein in relation to alkyl substituted phenols, the alkyl group can be methyl, ethyl n-propyl, isopropyl, n-butyl, isobutyl, secondary butyl and tertiary butyl. Specific examples of alkyl substituted phenols include: 2,6-dimethyl phenol, 2,4-dimethyl phenol, 2,4,6-trimethyl phenol, 2-tertiarybutyl-4-methyl phenol and 2,6-diisopropyl-4-methyl phenol.

More particularly, the diphenyl and di(alkyl substituted)phenyl peroxydicarbonate stabilizers contemplated herein can be represented by the following graphic formula IV:

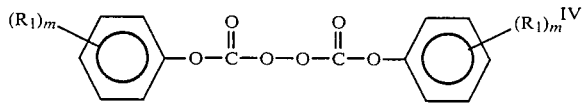

wherein $R_1$ and m are as defined above. As used herein, the terms diphenyl peroxydicarbonate stabilizer or a diphenyl peroxydicarbonate or diphenyl peroxydicarbonates are intended to refer to the compounds of graphic formula IV unless the specific compound diphenyl peroxydicarbonate is clearly indicated in the context of the disclosure.

The diphenyl peroxydicarbonate stabilizer is added to an aqueous organic peroxide dispersion as an antioxidant additive in stabilizing amounts, i.e., an amount that is sufficient to prevent substantial loss of the organic peroxide during storage. It is contemplated that a stabilized aqueous organic peroxide dispersion is one which loses less than about 10 percent of the initial organic peroxide concentration over a period of 30 days when stored at 0° to 5° C. More particularly, between about 0.05 and about 1 mole percent, more typically between about 0.05 and about 0.50 mole percent, of the diphenyl peroxydicarbonate, basis the organic peroxide in the aqueous dispersion, is used. The exact amount of diphenyl peroxydicarbonate required to stabilize the dispersed peroxide against homolytic decomposition will vary and depend not only on the diphenyl peroxydicarbonate used but also on the organic peroxide present in the dispersion. Determination of the suitability of a particular diphenyl peroxydicarbonate for a selected peroxide dispersion and the amount required to stabilize the peroxide can be effected by preparation of the stabilized peroxide dispersion and comparing its shelf life against the aforesaid standard.

The diphenyl peroxydicarbonate can be added to the organic peroxide by any suitable method, e.g., it can be dissolved in a suitable carrier solvent, e.g., an aliphatic alcohol such as $C_1$-$C_8$ alkanols, and the resulting solution added to the peroxide to be dispersed. Other carrier solvents which can be used include benzene, toluene, odorless mineral spirits, or any other solvent (hydrocarbon or otherwise) which is used to form solutions of the peroxide dispersed in the aqueous dispersion. It is preferred that the peroxide and diphenyl peroxydicarbonate be in the same phase.

When the organic peroxide dispersed is an organic peroxydicarbonate or organic peroxymonocarbonate ester, it is contemplated that the diphenyl peroxydicarbonate stabilizer can be formed "in situ" during synthesis of the peroxycarbonate ester by adding the phenyl (or alkyl substituted phenyl) chloroformate to the chloroformate precursor of the peroxycarbonate ester. Alternatively and preferably, the diphenyl peroxydicarbonate can be added to the chloroformate precursor of the peroxycarbonate ester prior to synthesis of said peroxycarbonate ester.

The present invention can be applied to aqueous dispersions of organic peroxides that are useful as initiators for the free radical polymerization of ethylenically unsaturated materials and particularly to the polymerization of such materials in an aqueous medium, e.g., a suspension, solution or emulsion polymerization. Preferably, the organic peroxide is a liquid at 0° C. and more preferably is a liquid at −5° C. Still more preferably, the organic peroxide is liquid at from −10° to −20° C. When the peroxide is a liquid at the temperatures the dispersion is formed and stored, the resulting peroxide dispersion is more commonly referred to as an emulsion. When the peroxide is a solid at the aforesaid temperatures, the resulting peroxide dispersion is more commonly referred to as a suspension. For convenience herein, the term dispersion is used to refer to both an emulsion and a suspension.

Examples of organic peroxides contemplated for use in the present invention are organic peroxydicarbonate esters, organic peroxymonocarbonate esters, diacyl peroxides and organic peroxyesters. The organic peroxydicarbonate esters can be represented by the following graphic formula:

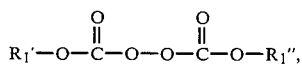

wherein $R_1'$ and $R_1''$ are each alkyl radicals of from 1 to 20 carbon atoms, e.g., 2 to 12 carbon atoms. In particular, $R_1'$ and $R_1''$ are alkyl radicals having from 2 to 8, e.g., 3 to 4, carbon atoms. More particularly, $R_1'$ and $R_1''$ can be the same or different, aliphatic or cycloaliphatic, branched or straight chain, and substituted and unsubstituted. Examples of $R_1'$ and $R_1''$ are methyl, ethyl, n-propyl, isopropyl, n-butyl, isobutyl, secondarybutyl, tertiarybutyl, capryl, 2-ethylhexyl, cyclohexyl, 4-tertiarybutylcyclohexyl, 3-methoxybutyl, 2-ethoxyethyl, myristyl, cetyl, stearyl, and 4-tertiaryamylcyclohexyl. Preferably, the peroxydicarbonate ester is di-n-propyl peroxydicarbonate, diisopropyl peroxydicarbonate, di-secondarybutyl peroxydicarbonate and di-2-ethylhexyl peroxydicarbonate. Mixtures of peroxydicarbonates can also be used to prepare the organic peroxide dispersion.

Peroxydicarbonate esters are well-known in the art and many are commercially available. Peroxydicarbonate esters are prepared typically by reacting the corresponding alkyl chloroformate with aqueous sodium peroxide at low temperatures, e.g., 0° C.-10° C., as described, for example, in the Journal of American Chemical Society, Volume 72, page 1254 (1950) and in U.S. Pat. No. 2,370,588.

Examples of organic peroxymonocarbonate esters contemplated are those represented by the following graphic formula:

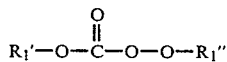

wherein $R_1'$ and $R_1''$ are as defined above. Preferably $R_1''$ in formula VI is a tertiary alkyl, e.g., $C_4$-$C_6$ tertiary alkyl radical and $R_1'$ is a lower alkyl, e.g., $C_1$-$C_6$ alkyl, radical. Of particular interest is tertiarybutylperoxy or tertiaryamylperoxy isopropylmonocarbonate. The above peroxymonocarbonate esters are known in the art and can be prepared by reacting the corresponding alkyl chloroformate, i.e.,

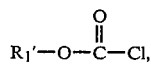

(e.g., isopropyl chloroformate) with the corresponding alkyl hydroperoxide, i.e., $R_1''$—O—O—H, (e.g., tertiarybutyl hydroperoxide) in the presence of an acid acceptor. See page 1259 and 1261 of the aforesaid J.A.C.S. article.

Examples of diacyl peroxides contemplated are those represented by the following graphic formula:

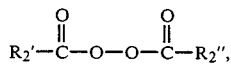

wherein $R_2'$ and $R_2''$ are each alkyl radicals of from 1 to 20, particularly 1-12, and more particularly 2-4, carbon atoms, or an aromatic or halo-substituted aromatic radical of from 6 to 8 carbon atoms. Thus $R_2'$ and $R_2''$ can each be methyl, ethyl, n-propyl, isopropyl, n-butyl, secondarybutyl, heptyl, nonyl, phenyl, halosubstituted phenyl, e.g., chlorophenyl and 2,4-dichlorophenyl, undecyl, octyl, etc. Of particular interest is diisobutyryl peroxide. Examples of other diacyl peroxides include: acetyl peroxide, benzoyl peroxide, caprylyl peroxide, p-chlorobenzoyl peroxide, decanoyl peroxide, 2,4-dichlorobenzoyl peroxide, lauroyl peroxide, pelargonyl peroxide, propionyl peroxide, didecanoyl peroxide, and dimyristoyl peroxide. Diacyl peroxides are prepared commonly by treating the appropriate acid chloride or anhydride with sodium peroxide or with hydrogen peroxide in the presence of a base, e.g., pyridine. See, for example, Organic Peroxides, Volume I, page 65, D. Swern, Ed., John Wiley & Sons, New York, 1970.

Examples of peroxyesters contemplated are the alkyl and alphacumyl esters of peroxycarboxylic acids, the acid portion of which contains from 3 to 13 carbon atoms. The alkyl ester portion of the peroxyester usually contains 4 or 5 carbon atoms, e.g., the tertiarybutyl or tertiaryamyl radical. The aforesaid peroxyesters can be represented by the following graphic formula:

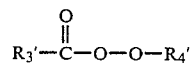

wherein $R_3'$ is an alkyl radical of from 2 to 12, e.g., 5 to 10, carbon atoms and $R_4'$ is an alkyl radical of 4 or 5 carbon atoms, most typically, the tertiarybutyl or tertiaryamyl radical, or the alpha cumyl radical. Examples of such peroxyesters include tertiarybutylperoxy pivalate, tertiaryamylperoxy pivalate, tertiarybutylperoctoate, tertiarybutyl perneodecanoate, tertiarybutylperoxy acetate, tertiarybutylperoxy isobutyrate, tertiarybutylperoxy-2-ethylhexanoate, tertiarybutylperoxy-3,5,5-trimethylhexanoate, tertiarybutyl peroxybenzoate, tertiaryamyl peroxyneodecanoate, and alphacumyl perneodecanoate. The aforesaid peroxyesters are typically prepared by treating the corresponding alkylhydroperoxide with an acylating agent.

In accordance with the present invention, a dispersion (emulsion or suspension) of the organic peroxide is prepared by dispersing the peroxide in water with a suitable dispersing aid, e.g., a surfactant or emulsifying agent. It is contemplated that the dispersion can contain between about 10 and 65 weight percent, typically between about 15 and 60, and more typically between 20 and 60, e.g., 40, weight percent, of the peroxide. The diphenyl peroxydicarbonate stabilizer is added to the peroxide dispersion in stabilizing amounts, or it can be charged to the water containing the surfactant or to the organic peroxide before the dispersion is formed.

As manufactured and stored, it is likely that the peroxide dispersion will contain a high percentage of organic peroxide, e.g., 20 or 40 to 60 or 65 weight percent. When used as an initiator for the emulsion or suspension polymerization of, for example, vinyl chloride, the peroxide composition of the present invention can be added to the polymerization vessel in its concentrated form or it can be diluted, e.g., with water, for more precise monitoring of the amount of peroxide added to the polymerization reactor.

The preparation of aqueous organic peroxide dispersions is well-documented in the literature. See, for example, U.S. Pat. No. 3,988,261. Generally, the surfactant(s) is dissolved in the aqueous medium and the organic peroxide added to the water phase with agitation.

The order of addition of the two phases, i.e., whether the external phase is added to the internal phase or vice versa, is generally of no concern since a dispersion can be prepared by the well-known inversion technique. However, the unstable characteristics and hazards associated with large quantities or organic peroxides suggests that it is best for the peroxide to be the discontinuous phase. Consequently, it is recommended that the organic peroxide be added slowly to the water phase to form the aqueous dispersion.

The temperature at which the peroxide composition of the present invention is formed is not critical, but should be low enough to avoid loss of peroxide by homolytic decomposition. The specific temperature used will depend on the organic peroxide and difficulties associated with handling that peroxide at a given temperature. For highly reactive organic peroxides, it is recommended that the temperature of the aqueous medium during formation of the dispersion be in the range of between above about 0° C. and 20° C., preferably from about +5° C. to 10° C. In the event that the surfactant(s) require higher temperatures for dissolution in the aqueous medium, the surfactant-water solution should be cooled before the peroxide is added to it. In preparing the peroxide composition, deionized or distilled water will typically be used.

Equipment used to prepare the peroxide dispersion is similarly well known. Any of the well-known equipment which is capable of breaking up or dispersing the internal phase, e.g., organic peroxide, in the external phase, e.g., water medium, so that the particle size of the resulting dispersion is sufficiently small to retard coalesce and resulting breakdown of the dispersed phase can be used. The choice of emulsification equipment is governed chiefly by the apparent viscosity of the dispersion in all stages of manufacture, the amount of mechanical energy input required and heat exchange demands, all of which are well known to persons skilled in the art. Examples of agitators capable of providing the proper degree of agitation are mechanically rotated paddle and anchor-type agitators; propeller agitation, i.e., one or more propellers mounted on a common shaft; turbine agitation, i.e., the use of fixed baffles, either on the mixing tank wall or adjacent to the propellers. Colloid mills and homogenizers are also suitable. Heat removal from the dispersion as it is being formed should be used to maintain the temperature of the total liquid medium below a temperature at which the organic peroxide undergoes significant homolytic decomposition.

The viscosity of the compositions of the present invention can vary but should be sufficiently free flowing to be handled by normal pumping means, i.e., the composition should be pumpable so that it can be handled in standard liquid handling equipment. The viscosity will vary depending on the amount of organic peroxide (and consequently the amount of water) that is used. The viscosity can be increased by known techniques, such as by adding thickeners to the continuous phase, by increasing the amount of the internal phase or by reducing the particle size of the emulsion. Preferably, the viscosity will be less than 500 poises, more preferably not more than 100 poises.

The amount of dispersing aid or emulsifier (hereinafter surfactant) used in the preparation of the peroxide dispersions of the present invention can vary, however, an amount of surfactant is used which is sufficient to provide a well dispersed, stable (non-settling with time) peroxide dispersion, i.e., an emulsifying amount. As a consequence, the peroxide remains dispersed at its designated storage temperature over such storage periods as are normally encountered in conventional commercial usage. Typically, the surfactant represents between about 1 and about 10 weight percent, more usually between about 3 and about 7 weight percent, e.g., about 5 weight percent, of the total dispersion. The exact amount of surfactant required can be ascertained easily by simple trial and error techniques using the aforementioned ranges as a guideline. Since surfactants are relatively expensive materials, only that amount which is required to accomplish the desired result are commonly used.

The surfactant should be soluble in the water phase to the extent required to perform the intended function and should remain dissolved in the water phase at all temperatures at which the dispersion is stored or handled. The surfactant should have a low chemical reactivity, i.e., it should be chemically inert or compatible with the organic peroxide and the phenolic antioxidant, and preferably should be compatible chemically with the polymerization environment to which the organic peroxide dispersion is added.

The surfactant can be anionic, cationic, nonionic or amphoteric. More commonly, the surfactant will be anionic or nonionic, more typically nonionic. Combinations of two or more surfactants or colloids are commonly used. See, for example, U.S. Pat. No. 4,092,470. Cationic and anionic surfactants are not used together since one would offset the surfactant properties of the other. Selection of a particularly useful surfactant for a particular organic peroxide can be facilitated by referring to the polymerization in which the organic peroxide emulsion will be used. In the aqueous polymerization, i.e., emulsion or suspension polymerization, of ethylenically unsaturated materials, emulsifiers and surfactants are used to maintain the polymer product dispersed within the aqueous polymerization medium. Anionic surfactants are commonly used with emulsion polymerizations while nonionic surfactants find extensive use in suspension polymerizations.

The subject of emulsions is covered in detail in Volume 8, pages 117–154 in the Kirk-Othmer Encyclopedia of Chemical Technology, second edition, John Wylie and Sons, Inc. 1965. A typical list of emulsifiers are presented on pages 128–130 of the aforementioned article. That article is hereby incorporated in toto by reference. The subject of surfactants is also covered in Volume 19 of the aforementioned Encyclopedia of Chemical Technology on pages 507–593, which article is also herein incorporated by reference. A brief discussion of the anionic, cationic and nonionic surfactants described in the aforementioned article follows.

ANIONIC SURFACTANTS

Carboxylates

The carboxylate class of surfactants are represented principally by the soaps and aminocarboxylates. Soaps have the general composition, $(R_5COO)^-(M)^+$ wherein $R_5$ is an alkyl group, usually in the $C_9$–$C_{21}$ range and M is a metallic ion, e.g., alkali metal or alkaline earth metal such as sodium, potassium, magnesium, calcium, barium and iron, or hydrogen or an amine ion. The amine salts, i.e., wherein M is an amino group are excellent emulsifiers. Examples of $R_5COO^-$ groups include lauroyl, oleoyl, stearoyl, cocoyl, and tall oil acyl.

Sulfonates

The sulfonate class of surfactants can be represented by the general formula, $R_6SO_3M$, wherein $R_6$ is a hydrocarbon group in the surfactant molecular weight range and M is typically an alkali metal, e.g., sodium, ammonium or amine group. Generally, the sulfonates are alkylbenzenesulfonates, petroleum sulfonates, sulfosuccinates, naphthalenesulfonates N-acyl-N-alkyltaurates, -sulfoesters of fatty acids, or -olefin sulfonates.

The alkylbenzenesulfonates, i.e., $R_7C_6H_4SO_3M$, are widely used. $R_7$ is typically $C_4$-$C_{14}$ alkyl, e.g., dodecyl, tridecyl, or nonyl, and M is sodium, calcium, hydrogen, ammonium or triethanolamino. Dialkyl sulfosuccinates are generally available as the sodium salt. The alkyl portion of the ester are in the $C_4$-$C_{14}$ range, mainly the $C_4$-$C_8$ range.

Naphthalenesulfonates, $C_8C_{10}H_6SO_3M$, are generally the salts of alkylnaphthalenesulfonates, salts of sulfonated formaldehyde-naphthalene condensates, salts of naphthalenesulfonates, and salts of tetrahydronaphthalenesulfonates, $R_8$ is typically $C_3$-$C_9$ alkyl. M is usually sodium or hydrogen.

Sulfates and Sulfated Products

The sulfate surfactants are grouped generally into sulfated alcohols, sulfated natural fats and oils, sulfated acids, amides and esters, ethoxylated and sulfated alkylphenols and ethoxylated and sulfated alcohols. Alkyl sulfates, $R_9OSO_3M$, are useful as emulsifiers and dispersants in emulsion polymerization. $R_9$ is typically $C_8$-$C_{18}$ alkyl, e.g., lauryl, 2-ethylhexyl, cetyl, oleyl, and octyl; while M is alkali, alkaline earth metal, e.g., sodium, potassium or magnesium, ammonium, triethanolamino, or diethanolamino.

Sulfated natural fats and oils are generally derivatives of tallow, castor oil, sperm oil, coconut oil, cod oil, neats'-foot oil, peanut oil and soybean oil. Sulfated polyoxyethylene alkylphenols, $R_{10}C_6H_4(OCH_2CH_2)_nOSO_3M$, are efficient emulsifiers and dispersants. $R_{10}$ is usually $C_9$ (nonyl), or $C_{12}$ (dodecyl), n is 2 to 5 and M is as defined hereinbefore, e.g., sodium, ammonium or triethanolamino. Sulfated polyoxyethylene alcohols, $R_{11}(OCH_2CH_2)_nOSO_3M$ are also useful in emulsion polymerization. $R_{11}$ is usually $C_{12}$-$C_{14}$, e.g., lauryl, tridecyl, or myristyl, n is 1 to 4 and M is as defined hereinbefore, i.e., usually sodium, ammonium or triethanolamino.

Phosphate Esters

Alkylphosphate and alkyl polyphosphate surfactants are also used as polymerization emulsifiers. The alkyl portion typically varies from $C_8$-$C_{18}$. Di(2-ethylhexyl)-phosphate is typical of the orthophosphate esters, and a typical polyphosphate is $(2\text{-ethylhexyl})_5\text{-Na}_5(P_3O_{10})_2$.

NONIONIC SURFACTANTS

Nonionic surfactants can be classed into the following groups: ethoxylated alkylphenols, ethoxylated aliphatic alcohols, carboxylic esters, carboxylic amides and polyoxyalkylene oxide block copolymers.

Ethoxylated alkylphenols

These nonionic surfactants are prepared from $C_6$-$C_{12}$ alkyl substituted phenols. The number of moles of ethylene oxide per mole of hydrophobe (alkyl phenol) can vary between 1.5 and about 30. The weight percent of combined ethylene oxide is usually from 40-95 percent to achieve good water solubility, more typically 60-95 percent. Nonylphenoxypoly(ethyleneoxy)ethanol is an example of this type of material.

Ethoxylated Aliphatic Alcohols

These nonionic surfactants are generally prepared from $C_{12}$-$C_{18}$ alcohols or mixtures of alcohols of that chain length and the mole ratio of combined ethylene oxide to hydrophobe varies from about 1 to 50, more often from 4 to 20. Examples of alcohols that can be ethoxylated are lauryl, oleyl, cetyl, stearyl, tridecyl, myristyl, trimethylnonyl, $C_{12}$-$C_{15}$ primary linear and $C_{11}$-$C_{15}$ secondary alcohol.

Carboxylic Esters

Examples of these type of surfactants are the glycerol esters, polyethylene glycol esters, anhydrosorbitol esters, ethoxylated anhydrosorbitol esters, ethylene and diethylene glycol esters, propanediol esters and ethoxylated natural fats and oils. The glycerol esters are either mono or diglycerides of fatty acids, usually $C_{12}$-$C_{18}$ fatty acids. The polyethylene glycol-esters are also esters of fatty, rosin, and tall oil acids. The fatty acids also generally contain 12 to 18 carbon atoms.

The mono-, di- or triesters of sorbitan and fatty acids are the most typical commercially available fatty acid esters of anhydrosorbitol. Sorbitan is a mixture of anhydrosorbitols of which 1,4-sorbitan and isosorbide are the principal components. The fatty acids are typically the $C_{12}$-$C_{18}$ fatty acids. Ethoxylation of the sorbitan fatty acid esters leads to a series of more hydrophilic surfactants. The number of oxyethylene units per mole of ester varies usually between 4 and 20.

The ethylene glycol, diethylene glycol and 1,2-propanediol esters of fatty acids having 12 to 18 carbon atoms are also used as surfactants. Ethoxylated castor oil and lanolin derivatives are the significant volume products of the ethoxylated natural fats and oils.

Polyvinyl Alcohol

Polyvinyl alcohol (PVA) is a hydrophilic colloid resin prepared by the acid or alkaline hydrolysis of a vinyl polymer, usually poly(vinyl acetate). The molecular weight of the PVA depends of the molecular weight of the parent polymer. The degree of hydrolysis of the parent polymer will vary the properties of the PVA. For use as a water soluble surfactant, hydrolysis should be substantial, e.g., 65 percent or more of the acetate groups should be hydrolyzed. The weight average molecular weight of the parent poly(vinyl acetate) is reported to vary between 11,000 and 1,500,000.

Water-Soluble Cellulose Ethers

Water-soluble cellulose ethers can also be used as surfactants in the present process. The cellulose ethers of commercial importance can be classified into three types. They are: (1) ionic-carboxymethylcellulose, e.g., sodium carboxymethylcellulose, (2) hydroxyalkylcellulose, e.g., hydroxyethylcellulose and (3) nonionicalkylcellulose, e.g., methylcellulose.

Sodium carboxymethylcellulose is a hydrophilic colloid that is anionic in character and is useful for stabilizing emulsions. A derivative, sodium carboxymethylhydroxyethylcellulose, is less sensitive to precipitation by salt solutions and acid, and is also useful in preparing the emulsions of the present process. Hydroxyethylcellulose is the principal commercial hydroxyalkylcellulose; however, hydroxypropylcellulose can also be used. Examples of alkyl cellulose include methylcellulose and ethylcellulose. Other water-soluble ethers include methylhydroxypropylcellulose, ethylhydroxyethylcellulose and methylethylcellulose. The degree of substitution (the average number of hydroxyl groups of the three available in the anhydroglucose unit that have been substituted) of the aforementioned cellulose ethers is usually at least about 0.5 and preferably at least 0.8 in order to attain water solubility.

Other hydrophilic-organic colloids that can be used in the present process in addition to the surfactants include the vegetable and other gums, e.g., starch, gelatin, pectin, and sodium alginate; and, inorganic suspending agents, such as the clays, bentonites and other finely-divided solids. For ease of reference, all of the aforementioned ingredients used to emulsify the peroxide (other than water) will be referred to as surfactants.

CATIONIC SURFACTANTS

The hydrophilic moieties in cationic surfactants are usually the quaternary nitrogens. The quaternary ammonium salts can be categorized into dialkyldimethylammonium salts, alkybenzyldimethylammonium salts (chlorides), alkyltrimethylammonium salts and alkylpyridinium halides. The quaternary salts are usually halides, e.g., chlorides or bromides, sulfates or sulfonates.

The organic peroxide dispersion can contain other materials which are added to prevent segregation of solid organic peroxide, e.g., thickeners, and materials capable of lowering the freezing point of the dispersion to permit the dispersion to remain liquid and easily pumpable at temperatures below 0° C.

As thickeners, there can be used the water-soluble cellulose ethers such as carboxymethylcellulose, heretofore described, polyvinylalcohol, polyvinylpyrrolidone, polyacrylic acid, carboxyvinylpolymers, geletin, starch, agar, etc. Depending on the type of thickener, the desired viscosity of the dispersion, the nonionic emulsifier used and the solid peroxide, the amount of thickener incorporated into the dispersion can be in the range of from about 0.05 to about 10 percent by weight. More typically, the amount of thickener incorporated is in the range of from 0.2 to 4 percent by weight.

To reduce the freezing point of the dispersion, there can be added from about 2 to about 20 percent by weight of an alkanol having from 1 to 4 carbon atoms and/or an alkanediol having from 2 to 4 carbon atoms. See, for example, European patent application No. 32,757.

In preparing the organic peroxide dispersions of the present invention, it is convenient to dissolve the surfactant(s) and/or the protective colloid in water, and add the diphenyl peroxydicarbonate stabilizer and organic peroxide to the resulting surfactant solution. The order in which these substances are combined is not critical.

The water used to form the dispersion is usually deionized or demineralized and deionized water to prevent the introduction of contaminants into the system in which the emulsion is used. The amount of water used to prepare the dispersion will vary with the amount of peroxide, surfactant (and/or protective colloid), diphenyl peroxydicarbonate and other additives present in the dispersion. The remainder of the dispersion after accounting for all of the aforementioned specific ingredients will be water. Typically the amount of water in the dispersion will vary between about 35 and about 90 weight percent.

The peroxide compositions of the present invention can be stored at the recommended storage temperatures for the peroxide or at higher temperatures due to the presence of the diphenyl peroxydicarbonate stabilizer. Those peroxides which are relatively stable at ambient temperatures will require no additional temperature control. However, those peroxides which normally require refrigeration for storage, shipment, etc. can have those requirements moderated. Generally, the less stable peroxides, e.g., the percarbonates, are stored at about $-20°$ C. In accordance with the present invention, such materials can be stored at from $-20°$ C. to about $+20°$ C., more typically from $-5°$ C. to $+20°$ C., e.g., $-5°$ C. to $+5°$ C. or $+10°$ C.

The peroxide composition of the present invention can be charged directly to the polymerization vessel or, if desired, diluted, e.g., with water, before being introduced into such vessel. Since the compositions are liquid and non-segregating, i.e., they remain dispersed during storage, they can be pumped from storage to the point of end use. The peroxide composition is used in amounts predetermined to be sufficient to initiate and sustain the polymerization reaction. Typically, enough of the peroxide composition is charged to the polymerization vessel to provide therein from about 0.01 to about 3 weight percent of the peroxide, basis the ethylenically unsaturated monomer.

The stabilized organic peroxide dispersions described herein can be used to initiate the emulsion, solution or suspension homopolymerization or copolymerization of ethylenically unsaturated monomers. Examples of such monomers include the vinyl halides and vinylidene halides, such as vinyl chloride, vinyl bromide, vinyl fluoride, vinylidene chloride and vinylidene fluoride. Other monomers include those having at least one terminal $CH_2=C<$ vinyl grouping, such as esters of acrylic acid, e.g., methyl acrylate, ethyl acrylate, butyl acrylate, octyl acrylate, cyanoethyl acrylate, allyl acrylate and the like; esters of methacrylic acid, e.g., methyl methacrylate, butyl methacrylate, and the like; styrene and styrene derivatives, e.g., methyl styrene, vinyl toluene, chlorostyrene, and the like; vinyl acetate, vinyl propionate, vinyl stearate, vinyl benzoate, acrylonitrile, methacrylonitrile, ethyl vinyl benzene, vinyl naphthalene, vinyl ethers, acrylamide, diallyl fumarates and maleates, olefines, e.g., ethylene and propylene; diolefins, e.g., butadiene, isoprene, chloroprene, and the like; and other vinyl monomers of the types known to those skilled in the art.

The present process is more particularly described in the following Examples which are intended as illustrative only since numerous modifications and variations therein will be apparent to those skilled in the art.

EXAMPLE 1

An aqueous emulsion containing 30 weight percent of di-2-ethylhexyl peroxydicarbonate (EHP) was prepared by dissolving 1.0 gram of Vinol ®205 polyvinyl alcohol and 0.50 grams of HLB 10 ethoxylated nonyl phenol mixture in 67.9 grams of water. To the resulting surfactant mixture at $+5°$ C. was added 30.6 grams of EHP with agitation. The EHP assayed 98.10 weight percent di-2-ethylhexyl peroxydicarbonate.

An aqueous emulsion containing 60 weight percent of EHP was prepared in the same manner except that 1.0 grams of Vinol ®205 polyvinyl alcohol, 0.50 grams of HLB 10 ethoxylated nonyl phenol mixture, 37.3 grams of water, and 61.2 grams of EHP were used.

The 30% and 60% EHP emulsion were each placed in a stoppered glass flask and stored in a refrigerated container at 0° C. to +5° C. At various intervals over a period of 60 days, samples of each emulsion were removed and analyzed for EHP. The results obtained are tabulated in Table I.

TABLE I

| EHP Emulsion, Nominal Wt. % | Initial Assay, % EHP | Assay After Storage at 0° C. to +5° C. | | |
|---|---|---|---|---|
| | | 13 Days | 28 Days | 60 Days |
| 30% | 29.67 | 28.92 | 27.84 | 26.40 |
| 60% | 59.40 | 54.91 | 47.18 | 37.86 |

EXAMPLE 2

The preparative procedures of Example 1 were repeated except that the compound, diphenyl peroxydicarbonate (DPP) was added to samples of the 30% and 60% EHP emulsions. The results obtained are tabulated in Table II.

TABLE II

| EHP Emulsion Nominal Wt. % | DPP Added Mole % | Initial Assay, % EHP | Assay After Storage at 0° C. to +5° C. | | |
|---|---|---|---|---|---|
| | | | 7 Days | 18 Days | 45 Days |
| 30% | 0.10 | 29.60 | 29.49 | 29.80 | 29.40 |
| 60% | 0.10 | 58.72 | 58.10 | 56.51 | 48.35 |
| 60% | 0.50 | 59.25 | 58.67 | 58.34 | 55.87 |
| 60% | 1.0 | 60.13 | 59.43 | 59.84 | 58.59 |

The data of Tables I and II show that the 30% EHP emulsion containing 0.10 mole % DPP as a stabilizer was significantly more stable than a similar emulsion without DPP. The data also shows that the 60% EHP emulsion containing 1.0 mole % DPP was much more stable than a similar emulsion without DPP. Enhanced stability against homolytic decomposition was also provided the 60% emulsion with 0.10 and 0.50 mole % DPP.

EXAMPLE 3

The 30 percent EHP emulsion containing 0.10 mole percent DPP that was prepared in Example 2 was used to polymerize vinyl acetate. For comparison, vinyl acetate was also polymerized using a 40 percent EHP emulsion and undiluted (neat) EHP. The polymerizations were performed in the following manner.

Vinyl acetate (50 grams), 0.05 mole percent EHP basis the vinyl acetate monomer, and 100 grams of a 0.1 weight percent aqueous solution of Methocel E-50 suspending agent were charged to 28 ounce polymerization bottles which were chilled by an ice bath. The atmosphere inside the bottles was removed by passing argon through the mixture for three minutes. The bottles were then capped, sealed and secured in safety cages. The cages and bottles were placed in a constant temperature water bath maintained at 40° C. and the bottles tumbled at a rate of 30 revolutions per minute for four hours.

One bottle was removed from the water bath at the end of each hour. This bottle was opened immediately and the contents poured into a two liter beaker containing about 1500 milliliters of hot water (about 50°–60° C.). The resulting aqueous suspension was then heated to boiling to remove the unreacted vinyl acetate monomer. The precipitated polymer was collected, washed with distilled water and dried in a vacuum oven at room temperature for at least 24 hours.

The intrinsic viscosity (in toluene, 25° C.) of each dried product was determined and the molecular weight of each polymer product was calculated from the intrinsic viscosity according to the Mark-Houwink equation. Results obtained are tabulated in Table III.

TABLE III

| | Suspension Polymerization of Vinyl Acetate at 40° C. | | | | |
|---|---|---|---|---|---|
| Peroxydicarbonate, | Amt. (mole %) | Poly(vinylacetate) % Conversion (Molecular Weight, $10^5$) | | | |
| | | 1 hr. | 2 hr. | 3 hr. | 4 hr. |
| 1. EHP, (>98%) | 0.05 | 26(3.3) | 57(4.3) | 81(6.0) | 85(5.6) |
| 2. EHP emulsion 40% | 0.05 | 26(4.4) | 53(4.7) | 80(6.0) | 85(5.5) |
| 3. EHP emulsion, 30% with 0.1 mole % DPP | 0.05 | 25(2.9) | 62(3.8) | 83(4.6) | 85(4.2) |

The data of Example 3 show that the percent conversion of vinyl acetate by each of the EHP initiator compositions used is essentially the same over the period of the polymerization. The molecular weight of the poly(vinyl acetate) prepared with the DPP stabilized EHP emulsion is slightly less than with the other two initiators. The use of diphenyl peroxydicarbonate in the manner herein described therefore, also serves to control (lower) the molecular weight of the polymer produced—a result that is useful to polymer manufacturers who have a need to produce such materials.

Although the present invention has been described with reference to specific details of certain embodiments thereof, it is not intended that such details be regarded as limitations upon the scope of the invention except as and to the extent that they are included in the accompanying claims.

I claim:
1. A peroxide composition comprising:
   (a) from about 10 to about 65 weight percent organic peroxide dispersed in an aqueous medium containing sufficient surfactant to provide a stable dispersion, and
   (b) from 0.05 to 1 mole percent, basis the organic peroxide, of diphenyl peroxydicarbonate stabilizer represented by the graphic formula:

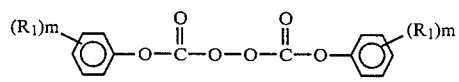

wherein $R_1$ is a $C_1$–$C_4$ alkyl and m is 0, 1, 2, or 3, said amount of diphenyl peroxydicarbonate being sufficient to reduce the rate of self induced homolytic decomposition of the organic peroxide at temperatures of from 0° C. to +5° C.

2. The peroxide composition of claim 1 wherein the diphenyl peroxydicarbonate stabilizer is diphenyl peroxydicarbonate.

3. The peroxide composition of claim 1 wherein the diphenyl peroxydicarbonate stabilizer is selected from the group consisting of di(2,6-dimethylphenyl) peroxydicarbonate, di(2,4-dimethylphenyl) peroxydicarbonate, di(2,4,6-trimethylphenyl) peroxydicarbonate, di(2-tertiarybutyl-4-methylphenyl) peroxydicarbonate, and di(2,6-diisopropyl-4-methylphenyl) peroxydicarbonate.

4. The peroxide composition of claim 1 wherein the organic peroxide is a peroxydicarbonate ester having the graphic formula:

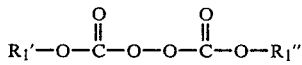

wherein $R_1'$ and $R_1''$ are each $C_2$–$C_{12}$ alkyl radicals.

5. The peroxide composition of claim 4 wherein the peroxydicarbonate ester is di-n-propyl peroxydicarbonate, di-isopropyl peroxydicarbonate, di-n-butyl peroxydicarbonate, di-secondary butyl peroxydicarbonate and di-2-ethylhexyl peroxydicarbonate.

6. The peroxide composition of claim 4 wherein the diphenyl peroxydicarbonate stabilizer is diphenyl peroxydicarbonate.

7. The peroxide composition of claim 1 wherein the organic peroxide is an organic peroxymonocarbonate ester, a diacyl peroxide, or an organic peroxyester.

8. The peroxide composition of claim 3 wherein the organic peroxide is a peroxydicarbonate ester having the graphic formula:

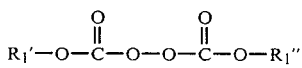

wherein $R_1'$ and $R_1''$ are each $C_2$–$C_{12}$ alkyl radicals.

9. The peroxide composition of claim 8 wherein the peroxydicarbonate ester is di-n-propyl peroxydicarbonate, di-isopropyl peroxydicarbonate, di-n-butyl peroxydicarbonate, di-secondary butyl peroxydicarbonate and di-2-ethylhexyl peroxydicarbonate.

10. The peroxide composition of claim 5 wherein the diphenyl peroxydicarbonate stabilizer is diphenyl peroxydicarbonate.

11. The peroxide composition of claim 10 wherein the diphenyl peroxydicarbonate is present in amounts of between 0.05 and 0.50 mole percent, basis the organic peroxide.

12. The peroxide composition of claim 10 wherein the organic peroxide is present in amounts of between 20 and 60 weight percent.

13. In the method of polymerizing ethylenically unsaturated monomers wherein an organic peroxide is used as an initiator for the polymerization, the improvement which comprises using as the organic peroxide a peroxide composition of (a) from about 10 to about 65 weight percent organic peroxide dispersed in an aqueous medium containing sufficient surfactant to provide a stable dispersion, and (b) from 0.05 to 1 mole percent, basis the organic peroxide, of diphenyl peroxydicarbonate stabilizer represented by the graphic formula:

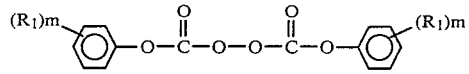

wherein $R_1$ is a $C_1$–$C_4$ alkyl and m is 0, 1, 2, or 3, said amount of diphenyl peroxydicarbonate being sufficient to reduce the rate of self induced homolytic decomposition of the organic peroxide at temperatures of from 0° C. to +5° C.

14. The method of claim 13 wherein the organic peroxide is a peroxydicarbonate ester having the graphic formula:

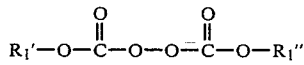

wherein $R_1'$ and $R_1''$ are each $C_2$–$C_{12}$ alkyl radicals, and wherein the diphenyl peroxydicarbonate stabilizer is diphenyl peroxydicarbonate.

15. The method of claim 13 wherein the organic peroxide is a peroxydicarbonate ester having the graphic formula:

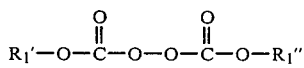

wherein $R_1'$ and $R_1''$ are each $C_2$–$C_{12}$ alkyl radicals, and wherein the diphenyl peroxydicarbonate stabilizer is selected from the group consisting of di(2,6-dimethylphenyl)peroxydicarbonate, di(2,4-dimethylphenyl)peroxydicarbonate, di(2,4,6-trimethylphenyl)peroxydicarbonate, di(2-tertiarybutyl-4-methylphenyl)peroxydicarbonate, and di(2,6-diisopropyl-4-methylphenyl)peroxydicarbonate.

16. The method of claim 14 wherein the peroxydicarbonate ester is di-n-propyl peroxydicarbonate, di-isopropyl peroxydicarbonate, di-n-butyl peroxydicarbonate, di-secondary butyl peroxydicarbonate and di-2-ethylhexyl peroxydicarbonate and the amount of diphenyl peroxydicarbonate stabilizer is from 0.05 to 1 mole percent, basis the peroxydicarbonate ester.

17. The method of claim 15 wherein the peroxydicarbonate ester is di-n-propyl peroxydicarbonate, di-isopropyl peroxydicarbonate, di-n-butyl peroxydicarbonate, di-secondary butyl peroxydicarbonate and di-2-ethylhexyl peroxydicarbonate and the amount of diphenyl peroxydicarbonate stabilizer is from 0.05 to 1 mole percent, basis the peroxydicarbonate ester.

18. The method of claim 16 wherein the ethylenically unsaturated monomer is vinyl chloride.

19. The method of claim 17 wherein the ethylenically unsaturated monomer is vinyl chloride.

20. The method of claim 13 wherein the organic peroxide is an organic peroxymonocarbonate ester, a diacyl peroxide, or an organic peroxyester.

21. The method of claim 20 wherein the diphenyl peroxydicarbonate stabilizer is diphenyl peroxydicarbonate.

22. The method of claim 13 wherein the organic peroxide is a peroxydicarbonate ester having the graphic formula:

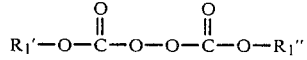

wherein $R_1'$ and $R_1''$ are each $C_2$–$C_{12}$ alkyl radicals.

* * * * *